United States Patent [19]
Spann

[11] 3,931,654
[45] Jan. 13, 1976

[54] LEG POSITIONER

[76] Inventor: Donald C. Spann, 5 Ferncreek Court, Greenville, S.C. 29607

[22] Filed: Nov. 4, 1974

[21] Appl. No.: 520,371

[52] U.S. Cl. .................... 5/327
[51] Int. Cl.[2] .................... A47C 21/00
[58] Field of Search .................... 5/327, 338; 269/325; 297/439, 427

[56] References Cited

UNITED STATES PATENTS

| | | | |
|---|---|---|---|
| 3,345,656 | 10/1967 | Steinman | 5/338 |
| 3,451,071 | 6/1969 | Whiteley | 5/338 |
| 3,505,994 | 4/1970 | Smith | 5/327 |
| 3,511,233 | 5/1970 | Holy, Jr. | 5/327 |
| 3,604,023 | 9/1971 | Lynch | 5/338 |
| 3,626,526 | 12/1971 | Viel | 5/338 |

*Primary Examiner*—Paul R. Gilliam
*Assistant Examiner*—Doris L. Trout
*Attorney, Agent, or Firm*—Bailey & Dority

[57] ABSTRACT

A device for positioning and supporting the lower leg and foot of a patient while lying on the side during periods of extended bedrest is formed from a block of polyurethane foam having resilient characteristics, and being of such configuration as to include a plurality of vertically extending sides between which an open arcuate groove extends longitudinally along the length of the block providing a cradle for the lower leg and a transverse slot extending across the vertical sides adjacent one end of the block for receiving a foot of a patient enabling the patient to lie on his side with the uppermost leg portion being positioned perpendicularly to the lower leg portion which is positioned perpendicularly to the foot.

3 Claims, 2 Drawing Figures

14
A
12
D

21
B
22
D
E
C
19
20
13
E
F
16
10
11
15
F
18
17

C
25
A
F
10
23
26
27
B
24

LEG POSITIONER

BACKGROUND OF THE INVENTION

It is often necessary to the therapy and comfort of a patient confined to bed for extended periods of time to bodily position the patient using various supporting and positioning devices usually such as pillows. When pillows are used, nurses spend an inordinate amount of time worrying about proper positioning, especially of older patients, and must spend additional time checking on the patient to make sure that the pillows haven't collapsed due to the patient moving.

In an attempt to provide better body positioning devices, foam rubber padding has been used to support the limbs of hospitalized patients such as shown in U.S. Pat. No. 3,345,656 wherein a lower limb is supported above the bed surface to prevent the formation of bed ulcers or bed sores on the heel which often result when the heel is allowed to contact the bed surface for prolonged periods of time. However, while such a device may be effective to support the patient's foot above the bed surface, such a device does not add support to the foot itself, nor does it provide for proper containment and support for the leg, ankle, and foot portions as a unit.

Accordingly, an important object of the present invention is to provide a device for supporting and positioning the lower leg and foot of a patient when lying on the side during prolonged periods of bed rest.

Another important object of the present invention is to provide a device for supporting and positioning the lower leg, ankle, and foot of a patient as a unit while the patient is lying on his side.

Another important object of the present invention is to provide a device for supporting and positioning a leg of a patient which will enable the patient to be positioned in a stable manner.

Another important object of the present invention is to provide a device for positioning and supporting the lower leg portion in a manner which is simple and requires very little time.

Another important object of the present invention is to provide a device for supporting and positioning the lower leg portion of a bed patient in a permanent manner so as to eliminate the inordinate amount of time a nurse spends checking on the bed patient and in repositioning the patient on the bed.

SUMMARY OF THE INVENTION

It has been found that a leg positioning device can be constructed of a resilient, deformable polyurethane foam block having an open arcuate groove extending along the entire length of the block providing a cradle for the lower leg portion, an open transverse slot extending across the block adjacent one end thereof for receiving a foot of a patient, and pressure sensitive fastening means located on each side of said slot and extending thereacross for adjusting the amount that the foot is gripped in the slot. Thus, the lower leg portion of a bed patient may be received and cradled in the open groove and the foot may be tilted and positioned as desired in the slot in a permanent and unitary manner by fastening the presure sensitive fastening means.

BRIEF DESCRIPTION OF THE DRAWINGS

The construction designed to carry out the invention will be hereinafter described, together with other features thereof.

The invention will be more readily understood from a reading of the following specification and by reference to the following specification and by reference to the accompanying drawings forming a part thereof, wherein an example of the invention is shown and wherein.

DESCRIPTION OF A PREFERRED EMBODIMENT

Figure 1:
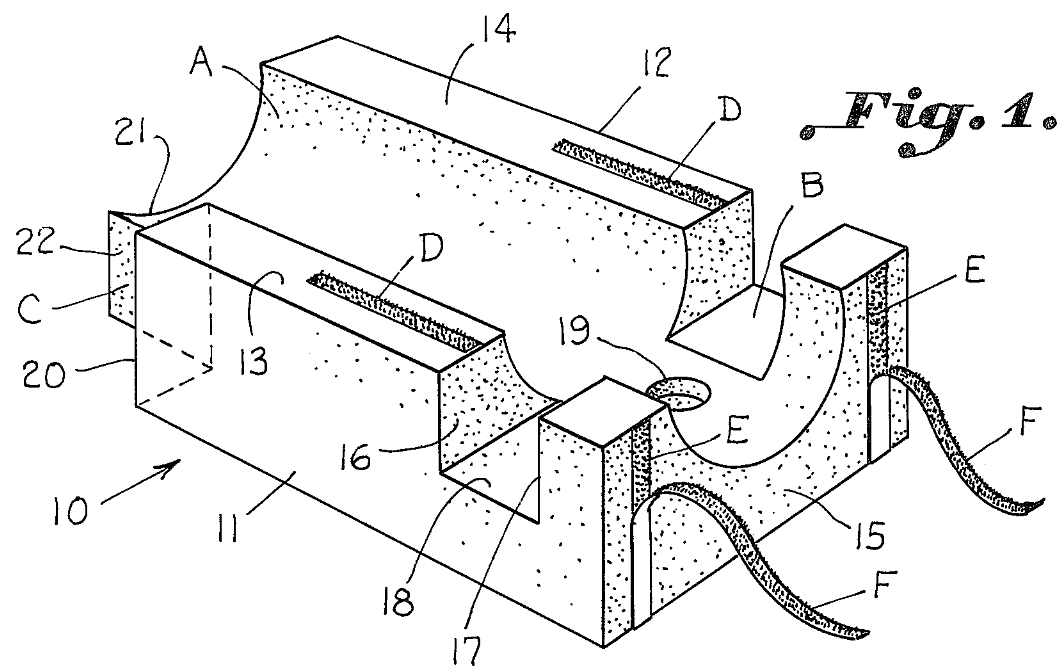
FIG. 1 is a perspective view illustrating a leg positioner constructed in accordance with the present invention.

The drawing illustrates a device for supporting and positioning the lower leg and foot of a patient as a unit when lying on the side during prolonged periods of bed rest.

An elongated positioning block, broadly designated at 10 is made of a resilient deformably polyurethane foam material which is lightweight and air-permeable. The block has the advantage of being inexpensive and suitable for one-patient use so that it does not have to be re-used. The block may be cut or sawed from a one-piece stock of foam material to provide a pair of vertically extending side portions 11 and 12 having top planar surfaces 13 and 14, respectively. An open arcuate groove A extends between the side portions 11 and 12 along the entire length of the block providing a cradle for receiving the leg portion of a patient. A transverse slot B extends across the block adjacent an end 15 of the block for providing a support for positioning of the patient's foot. The slot B may be of any cross-sectional shape, such as semicircular, but preferably is of a squared U-shape as shown. The slot is formed by cutting or sawing out a transverse section of the block and is defined by opposed vertically extending surfaces 16 and 17 and a flat bottom portion 18. Formed in the bottom portion 18 is a small circular cut-out 19 which receives the ankle portion (not shown) so as to substantially eliminate any pressure on the ankle.

Figure 2:
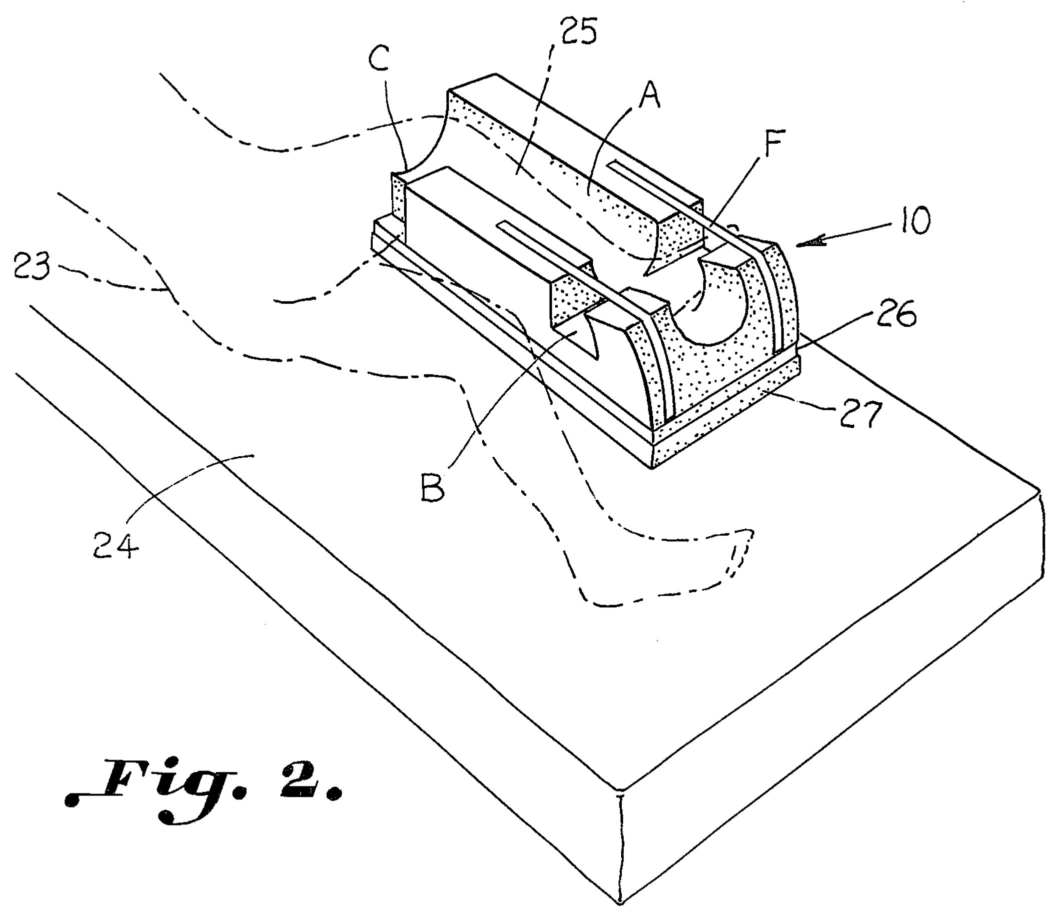
FIG. 2 is a perspective view illustrating a bed patient lying on a side whose lower leg portion is supported and positioned in a leg positioner constructed in accordance with the present invention.

The side portion 12 is continuous except for the square U-shaped opening formed therein by the slot B. The side portion 11 terminates at an end portion 20 which is short of the end portion 21 of the block 10 providing a corner cut-out portion C which is defined by the end portion 20 of side 11 and a vertical side surface 22 cut in the block 10 through part of the groove A. This cut-out portion at C alleviates any pressure on the back of the knee and also provides for supporting a lower portion of the patient's thigh as can be seen in FIG. 2. This provides additional support for the patient's knee portion preventing any discomfort due to side twisting of the knee joint.

A pressure sensitive fastening means preferably includes conventional Velcro strip members D,E, and F. The strip D is a hooking strip and is located on the top planar portions 13 and 14. A hooking strip E is located on the vertical surface of end portion 15 in alignment with the strips D. The strip member F is a pile strip which is hooked by strips E and D as it is placed there-over to provide a pressure sensitive fastening means. As the strip member F is fastened to the strips D and E, it extends over the slot portion B and provides for adjusting the closure of the slot and thus the gripping force against the patient's foot as held in slot B.

In use, the leg positioning block 10 may be used to support and position the lower leg portion and foot of a bed patient while lying on either side as best seen in FIG. 2. The body 23 of the patient is positioned on the left side on the bed surface 24 with the right lower leg portion 25 supported and positioned therein as a unit. This allows the patient to lie on his side with the leg unit positioned properly in a squared Z-shape when viewed from above. Thus, there should be a ninety degree angle from the patient's hip to the knee, the lower leg portion should be perpendicular to the knee, and the foot should be perpendicular to the lower leg portion or tilted slightly relative thereto. In this position the patient's lower thigh portion just above the knee, may be received in the cut-out portion C and rests upon the upper surface of the groove A to the extent desired. Therefore, the entire knee portion is supported by the leg positioning block. In this manner, the lower thigh portion, the knee, the lower portion, and the foot are supported and positioned in the block 10 as a unit which provides for the proper tensioning and relaxation of the muscles in the entire portion of the leg held therein. Hence, with the leg held as a unit, the problem of sagging muscles and cramping which often results from the inactivity of prolonged bed rest is reduced.

The Velcro strips D, E, and F are used to close the slot B to comfortably grip the patient's foot stabilizing the positioning of the patient's leg and preventing separation of the patient's leg and foot from the support block due to turning and the like.

With the patient's leg portion supported as a unit as described above, it is possible that the support block 10 may be moved back and forth on the bed surface to provide pumping of the leg portion for properly exercising the knee joint. This is advantageous when the patient is confined to bed for prolonged periods of time in order to keep the knee joint from becoming stiff and to keep the related muscles somewhat in shape. While the use of the leg positioning block 10 has been described with the patient lying on a side, it is possible that the body positioner can be used with the patient in a supine position supporting the lower leg and foot in a straight manner down the middle of the groove A.

It may also be desireable to use spacing blocks, such as 26 and 27 to raise and lower the position of the support block 10 to adjustably position the vertical distance of the patient's leg from the bed surface. The cut-out portion C may be located on either side 11 or 12 depending on whether the right leg or left leg is to be positioned, respectively. It is also possible that a single block could be used which incorporates a cut-out portion C in each of the vertical side members. However, when this is done support for the front of the knee is reduced. It is also possible that the positioning support block may be used without the cut-out portion C if only the upper ankle and foot portion are to be supported.

The device constructed in accordance with the present invention may be used advantageously to support and position a cast enclosed lower limb and foot of a side-positioned patient. In which case the drying of such a wet cast will be enhanced by the air-permeable characteristic of the foam material. This air flow capability also adds to the comfort of the patient's limb when supported without a cast.

While a preferred embodiment of the invention has been described using specific terms, such description is for illustrative purposes only, and it is to be understood that changes and variations may be made without departing from the spirit or scope of the following claims.

What is claimed is:

1. A device for supporting the lower thigh, leg and foot of a patient when lying on the side during prolonged periods of bed rest comprising:

a. an elongated base;

b. a plurality of sides extending upwardly from said base;

c. an open groove interposed between said sides extending the entire length of said base;

d. a pair of transverse surfaces in said sides adjacent one end of said base defining a transverse slot extending across said groove and said sides adjacent said one end thereof for receiving a foot of the patient when lying on the side; and e. pressure sensitive fastening means carried by a top surface extending between respective sides and said slot and by a vertical surface of said one end extending across said slot for adjustably closing said slot to position said foot supported therein;

whereby the patient may be properly positioned on a side with a knee bent, the lower portion of the leg cradled in said groove, and the foot tilted and positioned as desired in the slot by fastening the pressure sensitive fastening means in a desired position.

2. The structure of claim 1 wherein a corner of said elongated base is cut out for receiving the knee portion and alleviating pressure on a back upper portion of the patient's knee.

3. The structure of claim 1 wherein said base includes an opening in a bottom of said slot for receiving the ankle portion of said foot.

* * * * *